United States Patent [19]

Suarez

[11] Patent Number: 5,752,830
[45] Date of Patent: May 19, 1998

[54] REMOVABLE DENTAL IMPLANT

[76] Inventor: Omar F. Suarez, 30 Ferry St., Newark, N.J. 07105

[21] Appl. No.: 640,067

[22] Filed: Jun. 20, 1996

[51] Int. Cl.$^6$ ............................................. A61C 8/00
[52] U.S. Cl. ........................................ 433/173; 433/169
[58] Field of Search ................................ 433/169, 173, 433/174, 175

[56] References Cited

U.S. PATENT DOCUMENTS

| | | | |
|---|---|---|---|
| 3,955,280 | 5/1976 | Sneer | 433/169 |
| 4,324,550 | 4/1982 | Reuther et al. | 433/174 |
| 4,406,623 | 9/1983 | Grafelmann et al. | |
| 4,731,085 | 3/1988 | Koch | 433/173 |
| 4,863,383 | 9/1989 | Grafelmann | |
| 4,881,897 | 11/1989 | Franek et al. | 433/173 |
| 4,957,437 | 9/1990 | Shimura et al. | 433/174 |
| 4,960,381 | 10/1990 | Nixnick | |
| 5,049,073 | 9/1991 | Lauks | 433/174 |
| 5,114,343 | 5/1992 | Musikanti et al. | 433/173 |
| 5,135,395 | 8/1992 | Marlin | 433/174 |
| 5,213,500 | 5/1993 | Salazar et al. | 433/169 |
| 5,269,685 | 12/1993 | Jorneus et al. | |
| 5,269,686 | 12/1993 | James | |
| 5,312,255 | 5/1994 | Bauer | |
| 5,344,457 | 9/1994 | Pilliar et al. | |
| 5,372,503 | 12/1994 | Elia | |
| 5,468,150 | 11/1995 | Brammann | 433/169 |

FOREIGN PATENT DOCUMENTS 312935  4/1989  European Pat. Off. ........... 433/173

*Primary Examiner*—Ralph Lewis
*Attorney, Agent, or Firm*—Mathews, Collins, Shepherd & Gould

[57] ABSTRACT

A dental implant system has an inner housing removably received in an outer housing embedded in the bone for allowing a retentive screw or post retaining a prosthesis to be easily removed. A suspension mechanism provides lateral movement of the prosthesis for transferring forces from biting or chewing to the inside walls of the outer housing. A resilient coating on the inside wall of the inner housing absorbs the external forces. An interlocking gingival collar and abutment arrangement limit rotation of the prosthesis.

10 Claims, 3 Drawing Sheets

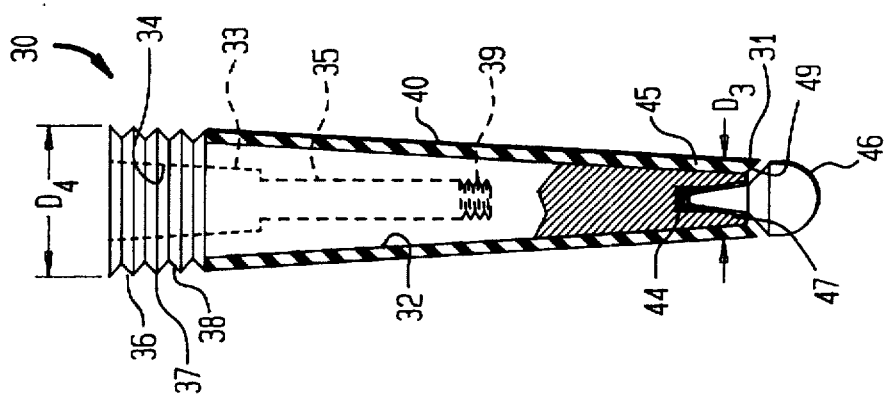
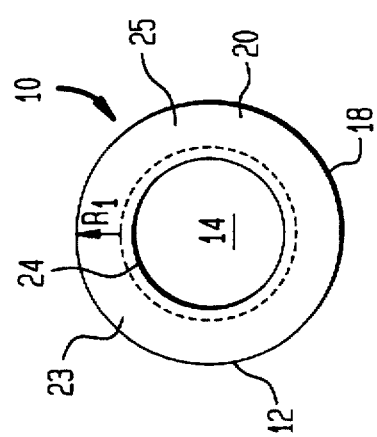
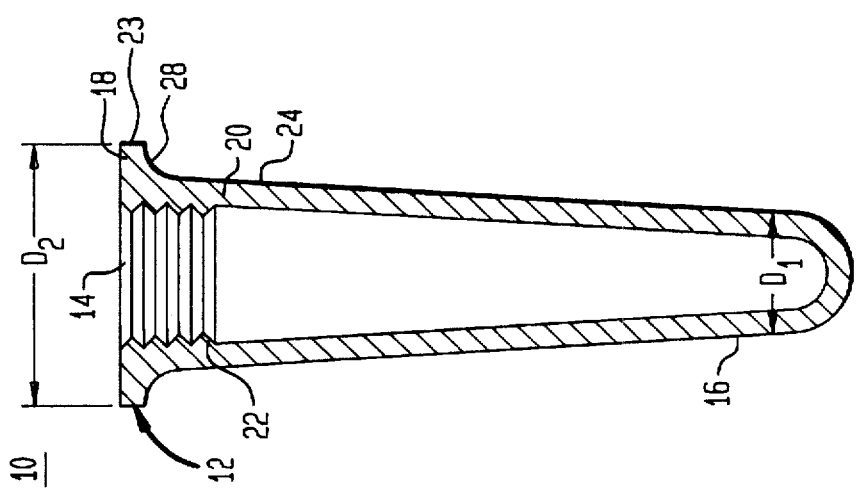

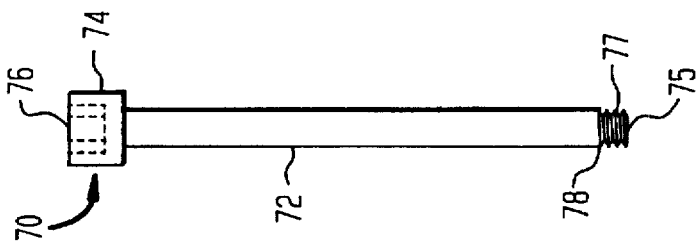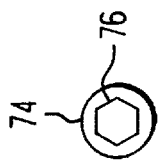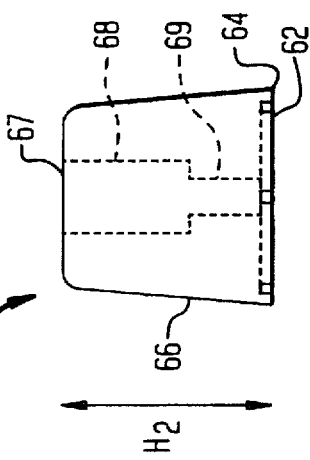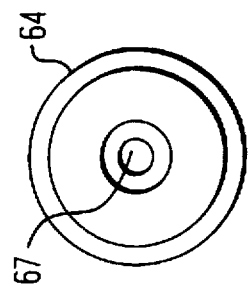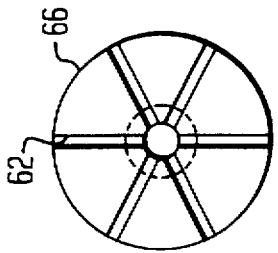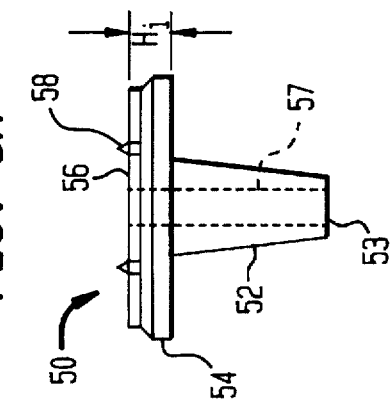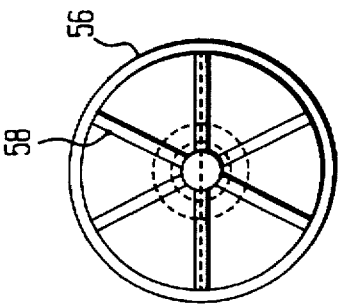

REMOVABLE DENTAL IMPLANT

BACKGROUND OF THE INVENTION

1. Field of the Invention

The invention relates to a dental implant in which an inner housing suspending a prosthesis is removably received in an outer housing implanted into the bone for expeditious alteration of the prosthesis.

2. Description of the Related Art

Dental implants for securing a dental prothesis to the bone are known. Typically, a hole is drilled in the bone. A biocompatible structure, such as titanium, is inserted into the hole. A threaded screw attaches the prothesis to the titanium structure. Several attempts have been made to improve the anchoring of the screw implant into the bone.

U.S. Pat. No. 5,269,686 describes a threaded drivable dental implant in which the implant is driven into a hole in the bone by forces exerted axially of the implant. When rotational forces are placed on the implant for attaching or removing the prothesis, long pitch threads of the implant mechanically resist the rotational forces.

U.S. Pat. No. 4,960,381 relates to a screw-type dental implant having an externally threaded self-tapping body portion for anchoring the implant. The body portion is linked at the top to a head portion. The head portion has a hexagonal shaped external wall surface for engagement with a wrench, such as an Allen-type wrench. The head portion has an outer circumference no greater than the circumference of the externally threaded body portion, thereby obviating any need to enlarge the top opening in the bone to permit insertion of the screw.

U.S. Pat. No. 4,863,383 describes an implant for dental purposes which contacts the bone at a wide area. The screw-in type bone implant has a post-receiving socket and a tapered shank which is integral with the socket. The implant is formed on the outside peripheral surface with self-tapping screw threads. The crest diameter of the screw tapping screw threads is not in excess of the diameter of a socket throughout the axial length of the screw threads. The socket receives a post which has a stem adapted to carry dental structures. Failures of the above described implants can be attributed to forces the implant receives during biting and chewing which are consequently transferred to the surrounding bone causing fracturing of the bone and loss of the implant.

A conventional attempt for enhancing bone attachment uses a porous surface implant to allow direct bonding of bone or soft connecting tissue without the need for threading of the bone. U.S. Pat. No. 5,344,457 describes an implant having a wide top portion connected to a tapered body portion. The lower bone engaging portion has a porous surface for anchoring the implant.

Another attempt is described in U.S. Pat. No. 5,372,503 in which an implant is loosely inserted into an opening in the bone. A packing composition is inserted into the opening to anchor the implant in the opening. The above described attempts having the shortcoming that the implant is permanent affixed to the bone and cannot be easily replaced.

Of possible general relevance are U.S. Pat. Nos. 5,312, 255; 4,406,623; 5,269,685 and 5,269,686.

It is desirable to provide an implant that is removable and can withstand forces applied during biting and chewing.

SUMMARY OF THE INVENTION

Briefly described, the present invention relates to a dental implant system for a jawbone in which posts or screws for attachment of an artificial tooth can be removed without surgical removal of the implant. The implant system has a removable inner housing which is slidably received in an outer housing. The outer housing is implanted into the jawbone. The inner housing is received in a cavity of the outer housing and can be removably coupled thereto. Preferably, the inner housing has a threaded upper portion which mates with a threaded upper portion of the outer housing for easy attachment of the inner housing to the outer housing.

In a preferred embodiment, the inner housing includes a suspension mechanism for absorbing external forces applied to the implant. Typically, the forces are lateral forces which arise from biting and chewing. The suspension mechanism can be formed of a pivoting apex at one end of the inner housing attached to a spring positioned within the inner housing. The inside surface of the inner housing can be formed of a resilient coating for absorbing forces from movement of the suspension mechanism.

A gingival collar slides into the upper portion of the inner housing. The collar can have a varied height to allow the implant to be aligned with different thicknesses of the gum. An abutment engages the gingival collar. Preferably, the abutment includes spokes which align with slots of the gingival collar to thereby reduce rotation of the abutment. A retentive screw passes through the abutment, gingival collar and screws into a bottom portion of the inner housing.

The invention will be more fully described with reference to the following drawings.

BRIEF DESCRIPTION OF THE DRAWINGS

FIG. 1A is a cross-sectional view of an outer housing of the dental implant system in accordance with the teachings of the present invention.

FIG. 1B is a top plan view of the outer housing shown in FIG. 1A.

FIG. 2 is a cross-sectional view of an inner housing of the dental implant system.

FIG. 3A is a side elevational view of a gingival collar of the dental implant system.

FIG. 3B is a top view of the gingival collar shown in FIG. 3A.

FIG. 4A is a side elevational view of an abutment of the dental implant system.

FIG. 4B is a top view of the abutment shown in FIG. 4A.

FIG. 4C is a bottom view of the abutment shown in FIG. 4A.

FIG. 5 is a side perspective view of a retentive screw which connects the abutment and gingival collar to the inner housing.

FIG. 6 is a top plan view of the retentive screw shown in FIG. 5.

DETAILED DESCRIPTION

Figure 7:
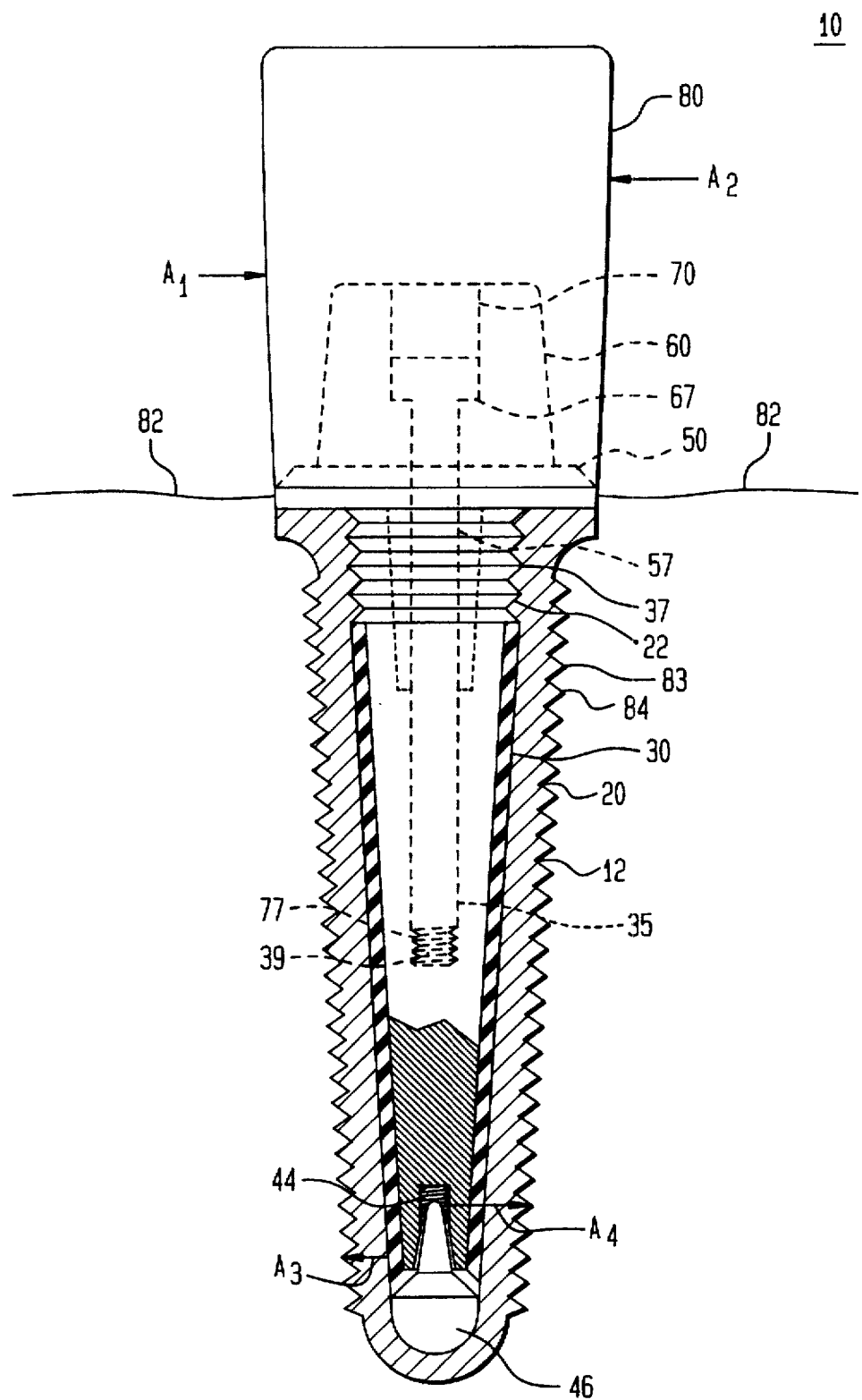
FIG. 7 is a perspective view of the dental implant system.

During the course of this description like numbers will be used to identify like elements according to the different figures which illustrate the invention.

FIG. 1A illustrates a cross-sectional view of an outer housing 12 used in the dental implant system 10 in accordance with the teachings of the present invention. Outer housing 12 is embedded into the alveolar bone of the jaw by drilling a hole in the bone and inserting outer housing 12. Cavity 14 is formed in outer housing 12. Preferably, outer housing 12 has a tapered shape. End 16 of outer housing 12 has diameter $D_1$ and end 18 of outer housing 12 has diameter $D_2$. Diameter $D_1$ is smaller than diameter $D_2$. The tapered shape of outer housing 12 provides easier placement into the bone with less bone being removed for insertion of the implant. The tapered shape anatomically matches the shape of the tooth root. Outer housing 12 is formed of a biocompatible material. Preferably, outer housing 12 is formed of a titanium alloy.

Internally threaded female portion 22 is positioned at upper portion 20 of outer housing 12. Top lip 23 extends a distance $R_1$ from body 24 of outer housing 12. Top lip 23 has a circular upper portion 25, as shown in FIG. 1B.

FIG. 2 illustrates inner housing 30 which is slidably received in cavity 14 of outer housing 12. Inner housing 30 has a tapered shape for matching the tapered shape of the outer housing 12. End 34 of inner housing 30 has diameter $D_3$ and end 31 of inner housing 30 has a diameter $D_4$. Diameter $D_3$ is smaller than diameter $D_4$. Upper portion 38 of inner housing 30 has externally threaded male portion 37 for mating with internally threaded female portion 22 of outer housing 12, thereby removably coupling outer housing 12 to inner housing 30. A collar receiving cavity 33 is formed within inner housing 30. Collar receiving cavity 33 has an upper tapered portion 34 and screw receiving aperture 35. Screw receiving aperture 35 has internally threaded female portion 39.

Spring suspension 44 is positioned at bottom end 45 of inner housing 30. Pivoting apex 46 is attached to end 47 of spring suspension 44. Pivoting apex 46 is seated in seat 49. Preferably, pivoting apex 46 is formed of metal. Pivoting apex 46 and spring suspension 44 provide lateral movement of spring suspension 44 towards inner wall 32 of inner housing thereby transferring forces from an attached prothesis to the inner wall 32 of the inner housing 30, which will be described in more detail below. Preferably, side wall 32 of inner housing 30 is formed of a coating of a resilient material. Most preferably, the resilient material can be formed of rubber or silicone. The resilient material absorbs forces from spring suspension 44.

FIGS. 3A and 3B illustrate gingival collar 50 which is coupled to inner housing 30. End 53 of post 52 of gingival collar 50 slides into upper tapered portion 34 of collar receiving cavity 33 of inner housing 30. Post 52 has a tapered shape for matching the tapered shape of upper tapered portion 34 of collar receiving cavity 33. Top 56 of lip 54 of gingival collar 50 is aligned with the surface of the gum. Lip 54 of gingival collar 50 can have a varied thickness $H_1$ for matching the thickness of the gum. For example, $H_1$ can be in the range of about 1 mm to about 5 mm depending on the thickness of the gum. Screw receiving aperture 57 is positioned within post 52 and lip 54.

Preferably, top 56 of gingival collar 50 has at least one protrusion 58 which surface is received in a matching slot of abutment 60, as shown in FIGS. 4A-4C. Slots 62 are formed in bottom 64 of abutment 60. In a preferred embodiment, top 56 of gingival collar 50 has a plurality of protrusions 58 in a spoked arrangement which are received in a corresponding plurality of slots 62 in abutment 60. The combination of protrusions 58 of gingival collar 50 and slots 62 of abutment 60 prevents abutment 60 from rotating by the application of external forces. Side 66 of abutment 60 has a height $H_2$ which protrudes above the gum. Screw receiving aperture 67 is formed in abutment 60. Screw receiving aperture has a top screw head receiving portion 68 and a bottom screw body receiving portion 69.

FIGS. 5 and 6 illustrate retentive screw 70 having body 72 and head 74. Preferably, head 74 has a hexagonal shaped indentation 76 for receiving a similar shaped screwdriver for attaching and removing retentive screw 70 from dental implant system 10. Body 72 has externally threaded male portion 77 at the bottom end 78 thereof.

FIG. 7 illustrates a perspective view of dental implant system 10. Inner housing 30 is slidably received in cavity 14 of outer housing 12. Internally threaded female portion 22 of outer housing 12 engages externally threaded male portion 37 of inner housing 30. Retentive screw 70 is inserted into screw receiving aperture 67 of abutment 60, screw receiving aperture 57 of gingival collar 50 and screw receiving aperture 35 of inner housing 30. Externally threaded male portion 77 of retentive screw 70 engages internally threaded female portion 39 of inner housing 30.

Prosthesis 80 is attached to abutment 60 and positioned above gum 82. In one embodiment, the outer surface 83 of outer housing 12 can include threaded portion 84 for screwing the outer housing 12 into the bone. Alternatively, outer surface 83 of outer housing 12 can be smooth.

Lateral force $A_1$ and $A_2$ can be applied to prosthesis 80 during chewing or biting. Lateral force $A_1$ result in movement of spring mechanism 44 in the direction $A_4$ and lateral force $A_2$ results in movement of spring mechanism 44 in the direction $A_3$.

In general, the present invention has the advantage of allowing a dental implant to be easily and expeditiously removed without surgically removing the implant from the bone. In addition, the tooth prosthesis is supported by a suspension mechanism for providing transferral of external forces from the prosthesis to the housing, thereby reducing stress on the retentive screw or post of the implant.

While the invention has been described with reference to the preferred embodiment thereof, it will be appreciated by those of ordinary skill in the art that modifications can be made to the structure and form of the invention without departing from the spirit and scope thereof.

I claim:
1. A dental implant system for a jawbone comprising:
   an outer housing adapted to be implanted into the jawbone, said outer housing being an elongated structure having a first end and a second end, said outer housing having a cavity therein between said first and second end and a cavity opening to said cavity at said first end, said outer housing having a tapered shape;
   an inner housing, said inner housing being an elongated structure having a first end and a second end, said first end of said inner housing being slidably received through said cavity opening into said cavity of said outer housing, said inner housing having a tapered shape matching said tapered shape of said outer housing;
   suspension means for suspending said inner housing in said cavity, said suspension means being positioned at said first end of said inner housing; and
   coupling means for removably coupling said second end of said inner housing to said first end of said outer housing;
   wherein said inner housing is adapted to be coupled to a prosthesis at said second end and said suspension means allows lateral movement of said inner housing towards said outer housing for transferring lateral forces applied to said prothesis to said inner housing.

2. The dental implant system of claim 1 wherein said suspension means comprises:

a seat positioned at said first end of said inner housing, said seat having a seat aperture therethough;

a pivoting apex received in said seat, said pivoting apex having a first end and a second end, a diameter of said first end of said pivoting apex seat aperture being larger than the diameter of said second end of said pivoting apex, said second end of said pivoting apex being received in said seat aperture and said diameter of said first end of said pivoting apex being larger than a diameter of said seat; and biasing means for biasing said pivoting apex, said biasing means being coupled to said second end of said pivoting apex.

3. The dental implant of claim 4 wherein said coupling means comprises:

an internally threaded female portion on an inner surface of said first end of said outer housing and an externally threaded male portion on an outer surface of said second end of said inner housing, said internally threaded female portion of said outer housing engaging said externally threaded male portion of said inner housing.

4. The dental implant system of claim 3 wherein said inner housing includes a collar receiving cavity between said first and second end and a collar opening to said collar receiving cavity at said second end of said inner housing and further comprising:

a gingival collar, said gingival collar having a lip and a post protruding from said lip, said post being slidably received through said collar opening to said collar receiving cavity.

5. The dental implant system of claim 4 wherein said lip of said gingival collar is adapted to abut the gum, said lip having a height $H_1$ which is in the range of about 1 mm to about 5 mm.

6. The dental implant system of claim 5 wherein an outer surface of said first end of said inner housing is formed of a resilient coating.

7. The dental implant system of claim 6 wherein said gingival collar has a collar screw receiving aperture formed within said lip and said post, said gingival collar having a first collar opening to said collar screw receiving aperture at said lip and a second opening to said collar screw receiving aperture at said post, said collar receiving cavity has a first end and a second end, a collar cavity screw receiving aperture formed at said first end of said collar receiving cavity, said collar screw receiving aperture having a screw opening at said first end further comprising:

an abutment, having a first end and a second end, said first end of said abutment being coupled to said lip of said gingival collar, said abutment having an abutment screw receiving aperture between said first end and said second end of said abutment, said abutment having a first abutment opening at said first end to said abutment screw receiving aperture and a second abutment opening to said abutment screw receiving aperture; and a retentive screw being received in said first abutment opening extending through said second abutment opening into said first collar opening extending through said second collar opening into said screw opening and into said collar screw receiving said aperture, said screw having a threaded body portion, said collar screw receiving aperture having an internally threaded female portion engaging said threaded body portion of said screw.

8. The dental implant system of claim 7 wherein, said gingival collar has at least one protrusion on said lip and said abutment has at least one slot at said first end for receiving said protrusion.

9. The dental implant system of claim 8 wherein said gingival collar has a plurality of protrusions which are received in a plurality of slots in said abutment.

10. The dental implant system of claim 9 wherein an outer surface of said outer housing is externally threaded for being adapted to be screwed into the bone.

* * * * *